(12) United States Patent
Haglund et al.

(10) Patent No.: US 10,184,923 B2
(45) Date of Patent: *Jan. 22, 2019

(54) CHROMATOGRAPHY COLUMN FRAME AND METHOD OF CONDUCTING MAINTENANCE ON AND PACKING OF A CHROMATOGRAPHY COLUMN

(71) Applicant: GE Healthcare Bio-Sciences AB, Uppsala (SE)

(72) Inventors: Bjorn Haglund, Uppsala (SE); Cheng Jiang, Shanghai (CN); Martin Kling, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,238

(22) Filed: Jan. 16, 2017

(65) Prior Publication Data

US 2017/0122919 A1    May 4, 2017

Related U.S. Application Data

(62) Division of application No. 14/409,446, filed as application No. PCT/SE2013/050744 on Jun. 21, 2013, now Pat. No. 9,566,538.

(30) Foreign Application Priority Data

Jun. 21, 2012  (CN) .......................... 2012 1 0236219

(51) Int. Cl.
  *B01D 15/22*    (2006.01)
  *G01N 30/60*    (2006.01)
  (Continued)

(52) U.S. Cl.
CPC ......... *G01N 30/6047* (2013.01); *B01D 15/10* (2013.01); *B01D 15/206* (2013.01);
(Continued)

(58) Field of Classification Search
CPC ........... G01N 30/6047; G01N 30/0021; G01N 30/6021; B01D 15/10; B01D 15/22
See application file for complete search history.

(56) References Cited

U.S. PATENT DOCUMENTS 5,213,683 A    5/1993  Mann
5,366,621 A   11/1994  Bidell
(Continued)

FOREIGN PATENT DOCUMENTS

DE    3833300         4/1990
DE    3833300 A1      4/1990
(Continued)

OTHER PUBLICATIONS

Office Action received for Japanese Patent Application No. 2015-518379, dated Feb. 21, 2017, 2 pages.
(Continued)

*Primary Examiner* — Eret C McNichols
(74) *Attorney, Agent, or Firm* — Wood IP LLC

(57) ABSTRACT

The invention relates to a chromatography column frame comprising at least two legs, a support arrangement connected to said at least two legs, and a holder means connected to said support arrangement. Said holder means is arranged to releasably hold an adaptor rod of a chromatography column, so that the adaptor rod is prevented to move in a horizontal direction and so the adaptor rod is allowed to move in a vertical direction. The invention also relates to method of conducting maintenance on and packing of a chromatography column.

6 Claims, 10 Drawing Sheets

(51) Int. Cl.
  *B01D 15/10* (2006.01)
  *G01N 30/56* (2006.01)
  *B01D 15/20* (2006.01)

(52) U.S. Cl.
  CPC ............ *B01D 15/22* (2013.01); *G01N 30/56* (2013.01); *G01N 30/6017* (2013.01); *G01N 30/6021* (2013.01); *G01N 2030/562* (2013.01); *Y10T 29/49721* (2015.01)

(56) References Cited

U.S. PATENT DOCUMENTS

| | | |
|---|---|---|
| 5,462,659 A | 10/1995 | Saxena |
| 5,667,675 A | 9/1997 | Hatch |
| 5,951,873 A | 9/1999 | Shalon |
| 6,001,260 A | 12/1999 | Hatch |
| 6,139,732 A | 10/2000 | Pelletier |
| 6,736,974 B1 | 5/2004 | Mann |
| 7,604,747 B2 | 10/2009 | Spencer |
| 7,671,203 B2 | 3/2010 | Antonini |
| 7,686,953 B2 | 3/2010 | Bailey |
| 7,780,853 B2 | 8/2010 | Davis |
| 7,785,473 B2 | 8/2010 | Davis |
| 8,066,876 B2 | 11/2011 | Hampton |
| 8,343,349 B2 | 1/2013 | Eriksson et al. |
| 8,470,173 B2 | 6/2013 | Maier-Rosenkranz |
| 8,562,826 B2 | 10/2013 | Bailey |
| 8,591,742 B2 | 11/2013 | Perreault |
| 8,663,477 B2 | 3/2014 | Uselius |
| 8,668,829 B2 | 3/2014 | Ramakrishna |
| 9,278,296 B2 | 3/2016 | Ramakrishna |
| 9,687,756 B2 * | 6/2017 | Lofving ................ B01D 15/22 |
| 2004/0164012 A1 | 8/2004 | Dunkley et al. |
| 2007/0138098 A1 | 6/2007 | Spencer |
| 2008/0290016 A1 | 11/2008 | Bailey et al. |
| 2008/0308498 A1 | 12/2008 | Davis |
| 2009/0039023 A1 | 2/2009 | Uselius |
| 2009/0078634 A1 | 3/2009 | Dunkley |
| 2010/0133165 A1 | 6/2010 | Bailey |
| 2011/0120951 A1 | 5/2011 | Hampton et al. |
| 2015/0198568 A1 | 7/2015 | Haglund et al. |
| 2017/0030872 A1 * | 2/2017 | Ramakrishna ......... B01D 15/22 |

FOREIGN PATENT DOCUMENTS

| | | |
|---|---|---|
| EP | 2324898 A2 | 5/2011 |
| EP | 2324898 B1 | 6/2013 |
| GB | 2325418 | 11/1998 |
| GB | 2325418 A | 11/1998 |
| GB | 2476320 | 6/2011 |
| JP | 2010-513873 A | 10/2007 |

OTHER PUBLICATIONS

International Search Report cited in corresponding application No. PCT/SE2013/050744, filed Jun. 6, 2013 (dated Oct. 17, 2013).
Supplemental European Search Report cited in EP Application No. 13807156.8 (dated Jan. 13, 2016).
Supplementary European Search Report issued in corresponding CN Application No. 201210236219.2.
Chinese Office Action dated Mar. 2, 2016 in CN Application No. 201210236219.2 (English Translation).
Chinese Search Report dated Feb. 23, 2016 in CN Application No. 201210236219.2 (English Translation).

* cited by examiner

CHROMATOGRAPHY COLUMN FRAME AND METHOD OF CONDUCTING MAINTENANCE ON AND PACKING OF A CHROMATOGRAPHY COLUMN

CROSS-REFERENCE TO RELATED APPLICATIONS

This is a divisional of U.S. patent application Ser. No. 14/409,446, filed Dec. 18, 2014, which is a national stage application under 35 U.S.C. § 371(c) of PCT application serial number PCT/SE2013/050744, filed on Jun. 20, 2013, which claims priority to Chinese patent application serial number 201210236219.2, filed on Jun. 21, 2012, the entire contents of which are incorporated by reference herein.

TECHNICAL FIELD

Embodiments of the present invention relate to a chromatography column frame and a method of conducting maintenance on and packing of a chromatography column.

Performing maintenance on chromatography columns, especially columns in industrial-scale chromatography, is necessary for cleaning and replacing bed supports, distributor plates and sliding rings. Heavy lifting equipment such as hoists or cranes to dismantle the columns has an influence on safety and time efficiency when performing maintenance. Also, when packing chromatography columns heavy lifting equipment such as hoists or cranes are often necessary. Embodiments of the invention are concerned with efficient and safer methods for performing maintenance on and packing of such columns.

BACKGROUND ART

The chromatography technique is widely used in different forms for separating chemical and biological substances and there are many applications in compound preparation, purification and analysis. Liquid chromatography is of particular importance in the pharmaceutical and biological industries for the preparation, purification and analysis of proteins, peptides and nucleic acids.

A typical liquid chromatography apparatus has an upright housing in which a bed of packing material, which is usually particulate in nature and consists of a porous medium, rests against a permeable retaining layer. A liquid mobile phase enters through an inlet, for example at the end of an adaptor rod which has an elongated extension within the column. The liquid mobile phase thereafter enters a distributor plate which distributes the liquid mobile phase through a porous, perforated filter, mesh, frit or net, which together with the distributor plate is arranged on an adaptor. The liquid mobile phase thereafter moves through the bed of packing material and is finally removed via an outlet, typically through a second filter, mesh, fit or net and a second distributor plate.

Columns used in liquid chromatography typically comprise a tubular body enclosing the porous chromatography medium through which the carrier liquid or mobile phase flows, with separation of substances or analytes taking place between the mobile phase and solid phase of the porous medium. Typically, the porous medium is enclosed in the column as a packed bed, generally formed by consolidating a suspension of discrete particles, known as slurry that is pumped or poured into the column when the uppermost, first end unit and the adaptor assembly have been removed. The production of a stable, even bed is often critical to the final separation process.

Conventional distribution systems for use in liquid chromatography comprise a distributor plate attached to the net. The distributor plate comprises channels arranged in a pattern to substantially uniform distribute the fluid over the plate. The distributor plate is perforated with holes or openings which lead the fluid from the channels and uniformly into the packed bed.

During the chromatography process the packed bed may be damaged and fines may occur in the column. After several chromatography cycles the fines may clog the net or nets in the column, which may result in higher back pressure and lower process efficiency. Therefore, maintenance of the chromatography columns must be conducted frequently and the nets or filters must be replaced after a number of cycles.

The backing plate or the lowermost, second end unit of the chromatography columns generally acts as a support for the column, being itself supported on legs or some other base arrangement positioned on the floor which allows clearance for outlet pipe work projecting beneath the column.

When such a column should be packed with a packing material and/or requires maintenance to, or cleaning of, internal components, such as the valves, seals, meshes/screens/filters, distribution systems etc., heavy lifting gear such as a crane or hoist is necessary to lift the uppermost, first end unit and the adaptor assembly away from the column tube and also the column tube away from the lowermost, second end unit as these assemblies can have e considerably weigh. The use of heavy overhead lifting equipment to disassemble the column in order to carry out internal maintenance is not desirable. Operator safety is obviously a concern when heavy equipment is lifted overhead and technicians exposed below. Furthermore, alignment structures are required to keep the column and its base/adaptor assemblies axially aligned as they are separated from each other, to avoid damage to the precision components.

The presence of such alignment and lifting structures imposes significant obstructions around the tube and need to be carefully laid out to provide sufficient clearance at some point of the circumference for insertion/removal of the internal components. Furthermore, the requirement to use heavy lifting equipment imposes constraints on housing such columns, sufficient overhead space and support being required to accommodate hoists or cranes. As many chromatography columns are now run in "clean" environments under GMP, to avoid microbiological contamination, where it is extremely difficult to accommodate overhead equipment, the requirement of moving the column to another room for disassembly, maintenance and/or packing is problematic. This problem is exacerbated by the need to clean and verify the column before returning it for use to the clean environment. The presence of hoists or cranes in GMP facilities used for biopharmaceutical manufacturing is thus highly undesirable for the above mentioned reasons, together with the fact that these machines shed particulate matter, in the form of dirt, during their operation and maintenance.

Document US 2004/0164012 A1 discloses a chromatography column that removes the longitudinal load from the column tube altogether and transfer it to a yoke and stanchion arrangement situated around but external to the column tube. By using the yoke and stanchion system a central adjuster can be used to move the top and end into and out of the housing. When internal pressure is applied to the column, the tube experiences no longitudinal load. The yoke and stanchion allow for complete removal of the end from the tube and provides a place to retain the end while the tube is being filed emptied, cleaned or repaired.

However, the chromatography column in US 2004/0164012 A1 has significant disadvantages associated with it by virtue of its design. As can be seen from US 2004/0164012 A1 the end is always connected to the yoke and the rest of the column and may therefore not be handled on separate places. Also, in order to remove the end from the interior of the column, the operator must lift the yoke and the end part to the retained state. As industrial columns typically have diameters ranging from about 200 mm to 2000 millimeters, this means that heavy lifts sometimes have to be performed. Therefore, maintenance and packing of the column disclosed in US 2004/0164012 A1 may thus be complicated and imposes a significant safety risk for the operator.

There are known chromatography columns provided with welded or heat shrinked nets on the distributor plate, which distributor plate in turn is removably connected by fastening elements on the adaptor. Time and cost consuming operations are necessary in order to remove the clogged net from the distributor plate. Especially, when the chromatography column is of a large size the removal of the net from the distributor plate by using milling or turning machines is complicated. The replaced net must be welded or heat shrinked on the distributor plate before remounting on the adaptor. The chromatography column may not be used under a substantially period of time during the replacement of the nets. This may lead to production losses in the pharmaceutical and biological industries.

Notwithstanding the existence of such prior art chromatography columns, there is a need to improve the maintenance and packing methods available for chromatography columns by providing columns which are safer and easier for operators to use. Also, there is a need to reduce cost and time when conducting maintenance on and packing of chromatography columns. Also, there is a need to reduce complexity and to reduce needed floor space when conducting maintenance on and packing of chromatography columns.

SUMMARY OF THE INVENTION

An objective problem to be solved by the present invention is to reduce cost when conducting maintenance on and packing of chromatography columns.

Another objective problem to be solved by the present invention is to reduce time when conducting maintenance on and packing of chromatography columns.

Still another objective problem to be solved by the present invention is to increase safety when conducting maintenance on and packing of chromatography columns.

Still another objective problem to be solved by the present invention is to reduce complexity when conducting maintenance and packing of on chromatography columns.

Still another objective problem to be solved by the present invention is to reduce needed floor space when conducting maintenance on and packing of chromatography columns.

These objects above are achieved by a chromatography column frame according to claim 1 and a method of conducting maintenance on and packing of a chromatography column described herein.

The chromatography column frame and the method according to an embodiment of the invention eliminates the need for heavy lifting gear such as a crane or hoist with surrounding equipment which increases the cost when conducting maintenance on and packing of chromatography columns. Also, the frame and the method provides for easier and less time consuming maintenance on chromatography columns because a number operation steps can be eliminated in comparison with known maintenance methods. Therefore, the efficiency when conducting maintenance on and packing of such column increases. The demand for a large floor space when dismantle the column is also eliminated by the frame and the method. The elimination of heavy lifting equipment, such as separate hoists or cranes to dismantle the column, increase safety to equipment and maintenance personnel when conducting maintenance on and packing of such columns.

An embodiment of the invention accordingly comprises the method of maintenance, the method of packing, the features of construction, combination of elements, and arrangement of parts that will be exemplified in the description set forth hereinafter and the scope of the invention will be indicated in the claims.

BRIEF DESCRIPTION OF THE DRAWINGS

Further aspects, advantages and features of the invention can be derived from the following detailed description of exemplary embodiments of the invention, with reference to the drawings.

DETAILED DESCRIPTION

Figure 1:
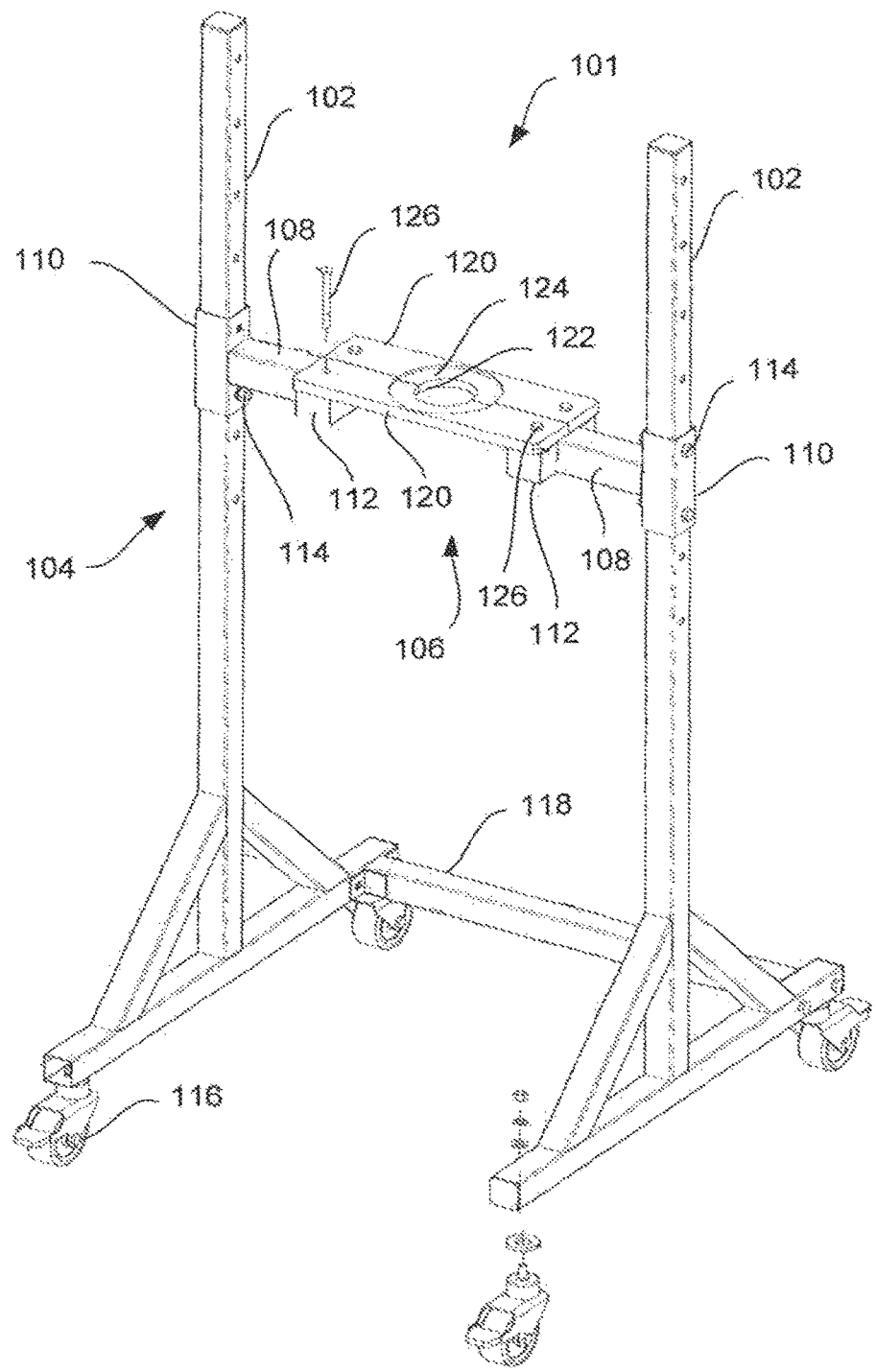
FIG. 1 shows a view in perspective of a chromatography column frame according to the present invention.

FIG. 1 shows a chromatography column frame 101 comprising least two legs 102, which are substantially vertically and arranged in parallel. A support arrangement 104 is connected to the legs 102 and a holder means 106 is connected to the support arrangement 104. The disclosed embodiment of the frame 101 in FIG. 1 is constructed of elongated steel tubes which have a square cross section. It is however also possible to design the frame 101 in other materials having other cross sections, for example a circular cross section. The support arrangement 104 comprises two substantially identical brackets 108 provided with a first and second connection means 112. The first connection means 110 is arranged to connect the bracket 108 with one of the legs 102 of the frame 101, and the second connection means 112 is arranged to be connected to the holder means 106. The support arrangement 104 is adjustable along said legs 102, so that the frame 101 may be adapted for chromatography columns of different sizes. Therefore, the first connection means 110 of the support arrangement 104 is releasably connected to the leg 102 by means of fastening elements 114. Wheels 116 are arranged on the frame 101, so that the frame 101 may be easily moved to and from the position of the chromatography column 128. The wheels 116 are lockable, so that the frame 101 is prohibited from moving on the floor surface when the wheels 116 are locked. A cross bar 118 is arranged between the legs 102 in order to increase the stabilisation of the frame 101.

The holder means 106 comprises at least one support plate 120 provided with a recess 122 and a bearing surface 124. In an embodiment, as disclosed in the embodiment in FIG. 1, two support plates 120 are arranged on the support arrangement 104, each plate is provided with a recess 122, which recesses 122 together define a substantially circular opening and a circular bearing surface 124 around the opening. At least one of the support plates 120 is removably connected to the second connection means 112 of the support arrangement 104 by means of fasteners 126, such as bolts or the like.

Figure 2:
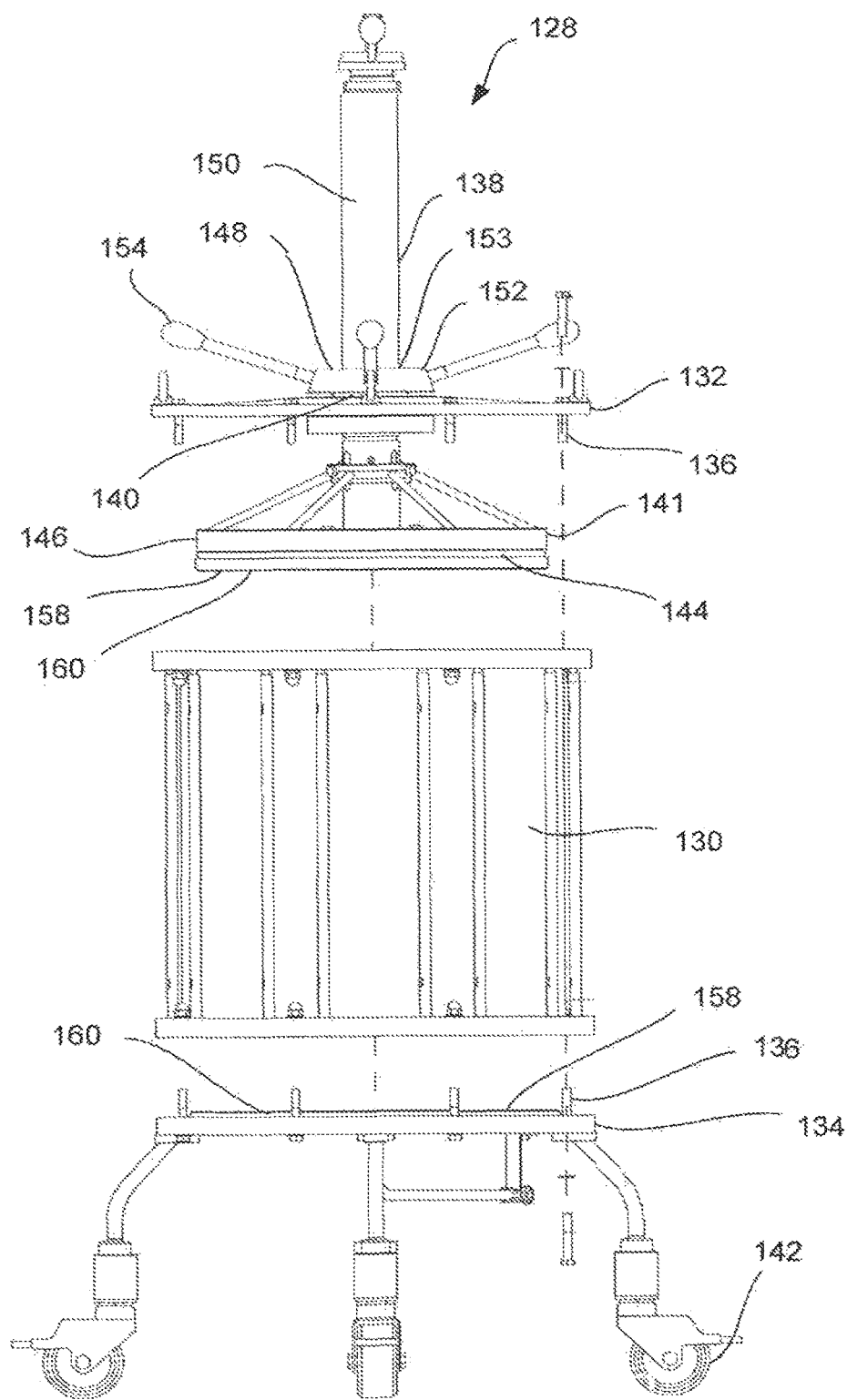
FIG. 2 shows a side view of the chromatography column with parts demounted and arranged at a distance from each others.

FIG. 2 shows a side view of a chromatography column 128 with parts demounted and arranged at a distance from each others. The chromatography column 128 comprises a tubular housing 130, a first end unit 132 and a second end unit 134, when secured together to form a fluid tight seal by means of tension bolts 136. The first and second end units 132, 134 are removably connected to the tubular housing 130 by means of the tension bolts 136. The tubular housing 130 and end units 132, 134 are typically composed of stainless steel or a high-strength plastic material such as polypropylene. In an embodiment, where the column 128 is to be used for the separation of biologically active substances, the material is biologically inert such that it does not elicit an immune response in humans in accordance with United States Pharmacopia (USP) <88> class VI. An adaptor rod 138 extends through an opening 140 in the first end unit 132 and into the tubular housing 130. The column 128 is arranged on supporting wheels 142, so that the column 128 may be easily moved to a suitable position on a floor. Instead of arranging the supporting wheels 142 directly on the second end unit 134 it is possible to provide a support trolley (not disclosed) with wheels in a position under the column 128.

An adaptor 141, which is connected to the adaptor rod 138, has a substantially circular shape provided with a sealing ring 144 on a peripheral outer surface 146, which is arranged to seal against the inner surface of the tubular housing 130 of the chromatography column 128. When lowering the adaptor 141 by means of an operating means 148, the packing material within the tubular housing 130 will be compressed and packed. In the disclosed embodiment the adaptor rod 138 is provided with an external thread 150 and the operating means 148 is a threaded collar 152 provided with handles 154 for manually pivoting of the collar 152. When pivoting the collar 152 the adaptor rod 138 will be displaced by means of the external thread 150 on the rod 138 and the internal thread 153 of the collar 152. The compression force and downward movement of the adaptor 141 in the tubular housing 130 is thus achieved by forcing the adaptor rod 138 downward by pivoting the collar 152.

A distributor plate 158 and a chromatography column filter 160 are mounted on the adaptor 141 and on the second end unit 134. The chromatography column filter 160 comprising, a porous, perforated net element through which fluid and particles up to a predetermined size are allowed to pass. Maintenance and cleaning of the filter 160 and the distributor plate 158 are necessary and therefore the filter 160 and the distributor plate 158 are, in an embodiment, removably fixated to the adaptor 141 and to the second end unit 134.

Figure 3:
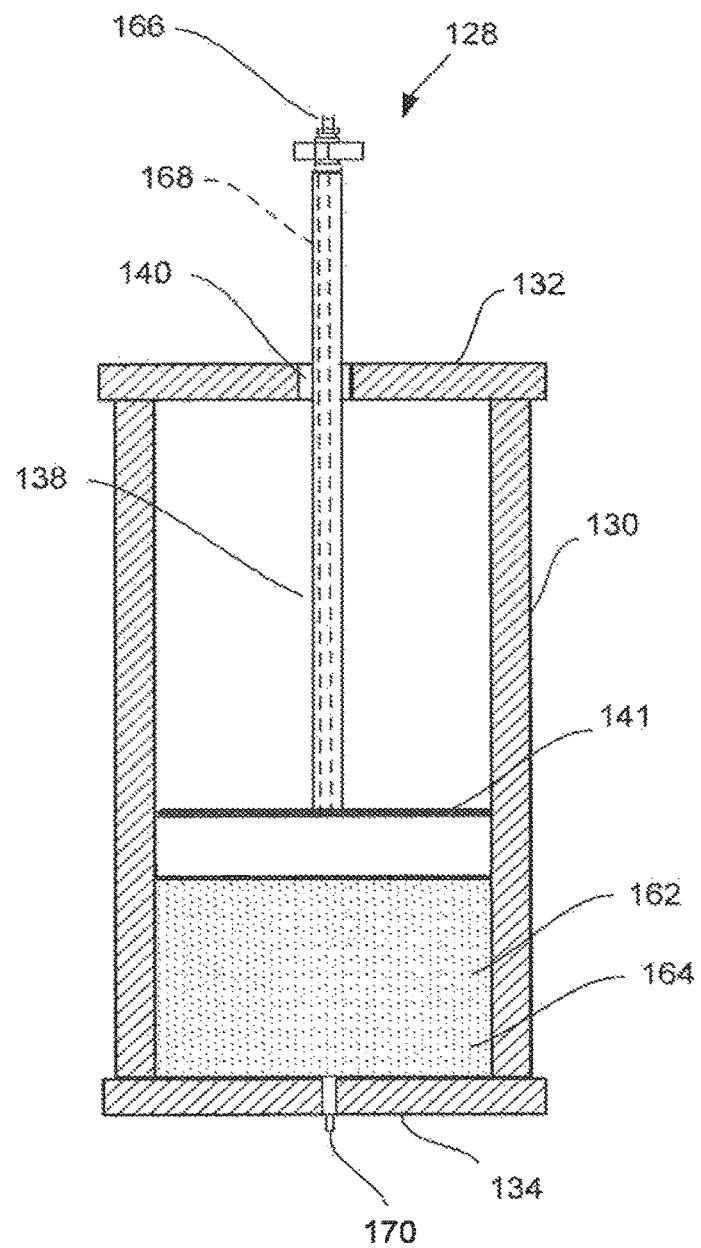
FIG. 3 shows a schematic section view of a chromatography column.

FIG. 3 shows a schematic section view of the chromatography column 128 in FIG. 1. The tubular housing 130, the second end unit 134 and the adaptor 141 form a bed space 162, which space is fluid tight and capable of withstanding high operating pressures. A wide range of column capacities is possible, typically ranging from 0.1 to 2000 liters. The bed space 162 is filled with a bed 164 of packing material, which is usually particulate in nature and consists of a porous medium. A liquid mobile phase is arranged to enter through an inlet 166 at the end of the adaptor rod 138 and flows through a central channel 168 in the adaptor rod 138 and further to the adaptor 141. The liquid mobile phase thereafter moves through the bed 164 of packing material and is finally removed via an outlet 170 in the second end unit 134. Typically, the porous medium enclosed in the column 128 as a packed bed 164 is generally formed by consolidating a suspension of discrete particles, known as slurry that is pumped or poured into the column 128 when the first end unit 132 and the adaptor have been removed from the tubular housing 130.

The bed 164 of packed particulate medium is obtained by the downward movement of the adaptor 141 to compress the bed 164 between the adaptor 141 and the second end unit 134. The compression force and downward movement of the adaptor 141 is achieved by forcing the adaptor rod 138 downward by using an operating means 148, which may be manually, electrically, hydraulically or pneumatically operated.

Figure 4:
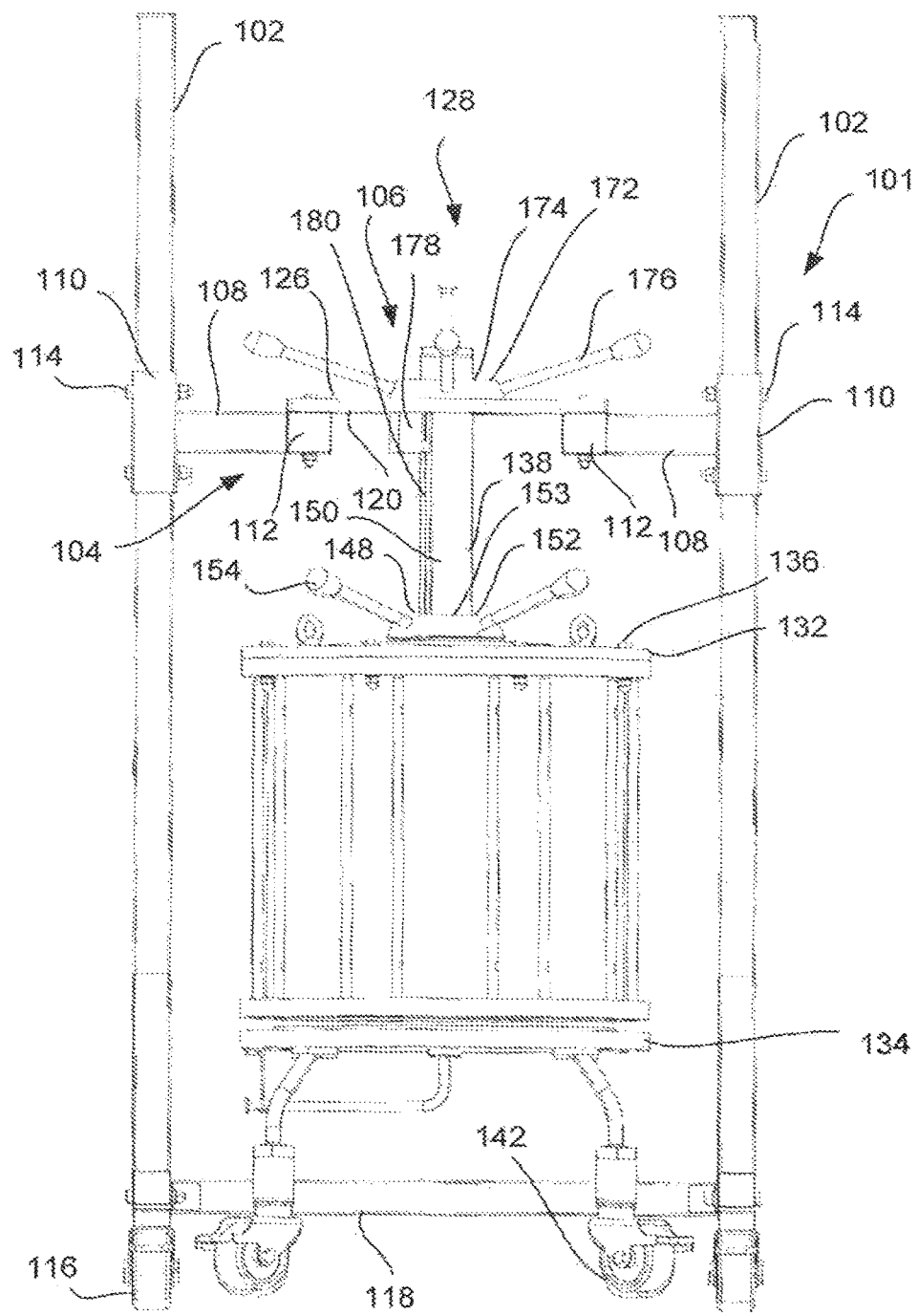
FIG. 4 shows a side view of the chromatography column in FIG. 2 positioned in the frame according to FIG. 1.

FIG. 4 shows a side view of a chromatography column 128 arranged in the frame 101 according to an embodiment. The holder means 106 is arranged to releasably hold the adaptor rod 138 of the chromatography column 128, so that the adaptor rod 138 is prevented to move in a horizontal direction and so the adaptor rod 138 is allowed to move in a vertical direction. This is achieved by the circular recess 122 formed by the two support plates 120 of the holder means 106. The recess 122 defines an opening for the adaptor rod 138 and the opening therefore has a larger dimension than the dimension of the adaptor rod 138. At least one of the support plates 120 is removably connected to the support arrangement 104 by means of fasteners 126, such as bolts or the like. Therefore, one of the support plates 120 is dismounted from the brackets 108 of the support arrangement 104 when positioning the column 128 into the frame 101. When the column 128 is in position the support plate 120 is mounted on the brackets 108 of the support arrangement 104 and the adaptor rod 138 of the column 128 is horizontally fixed by means of the support plates 120. The support plates 120 are provided with a bearing surface 124 for a driving means 172 arranged on the adaptor rod 138. The driving means 172 is a threaded sleeve 174 provided with handles 176 arranged to interact with the threads 150 on the adaptor rod 138, so that the adaptor rod 138 moves in the vertical direction when pivoting the sleeve 174.

A stopper means 178 is arranged on the support arrangement 104, which stopper means 178 is adapted to interact with an axial groove 180 in the adaptor rod 138, so that the adaptor rod 138 is prevented from pivoting in said holder means 106 when the sleeve 174 is pivoted. In an embodiment, the stopper means 178 is arranged on one of the support plates 120.

The method of conducting maintenance on and packing of a chromatography column 128 according to an embodiment of the invention comprises the steps of providing a chromatography column 128 and the frame 101 according to an embodiment of the invention. Thereafter, the first end unit 132 or the second end unit 134 is disconnected from the tubular housing 130 depending on the type of maintenance which should be performed or if the column 128 should be filed with packing material. The disconnection is achieved by removing the tension bolts 160 which connect the end units 132, 134 to the tubular housing 130.

Figure 5:
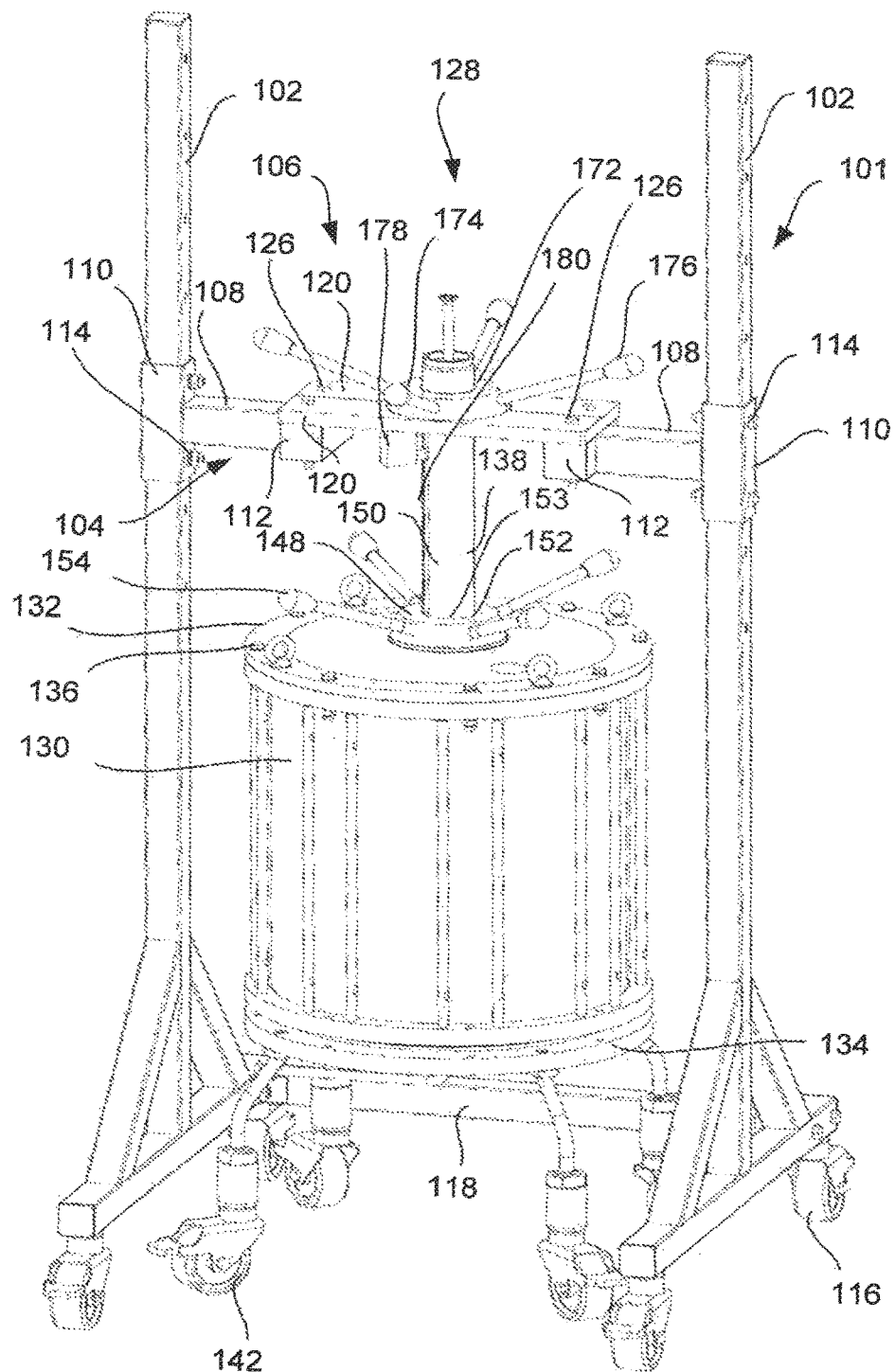
FIG. 5 shows a view in perspective of the chromatography column in FIG. 2 positioned in the frame according to FIG. 1.

As disclosed in FIG. 4 and also in a view of perspective FIG. 5 the adaptor rod 138 is positioned in the holder means 106, so that the adaptor rod 138 is prevented from moving in a horizontal direction and so the adaptor rod 138 is allowed to move in a vertical direction. Thereafter the driving means 172 is arranged on the adaptor rod 138 and the driving means 172 is activated, so that the adaptor rod 138 together with the first end unit 132 and the adaptor assembly 141 move vertically upwards separating the first end unit 132 and the adaptor assembly 141 from the tubular housing 130 or also separating the tubular housing 130 from the second end unit 134 depending on the type of maintenance which should be performed or if the column 128 should be filed with packing material.

Figure 6:
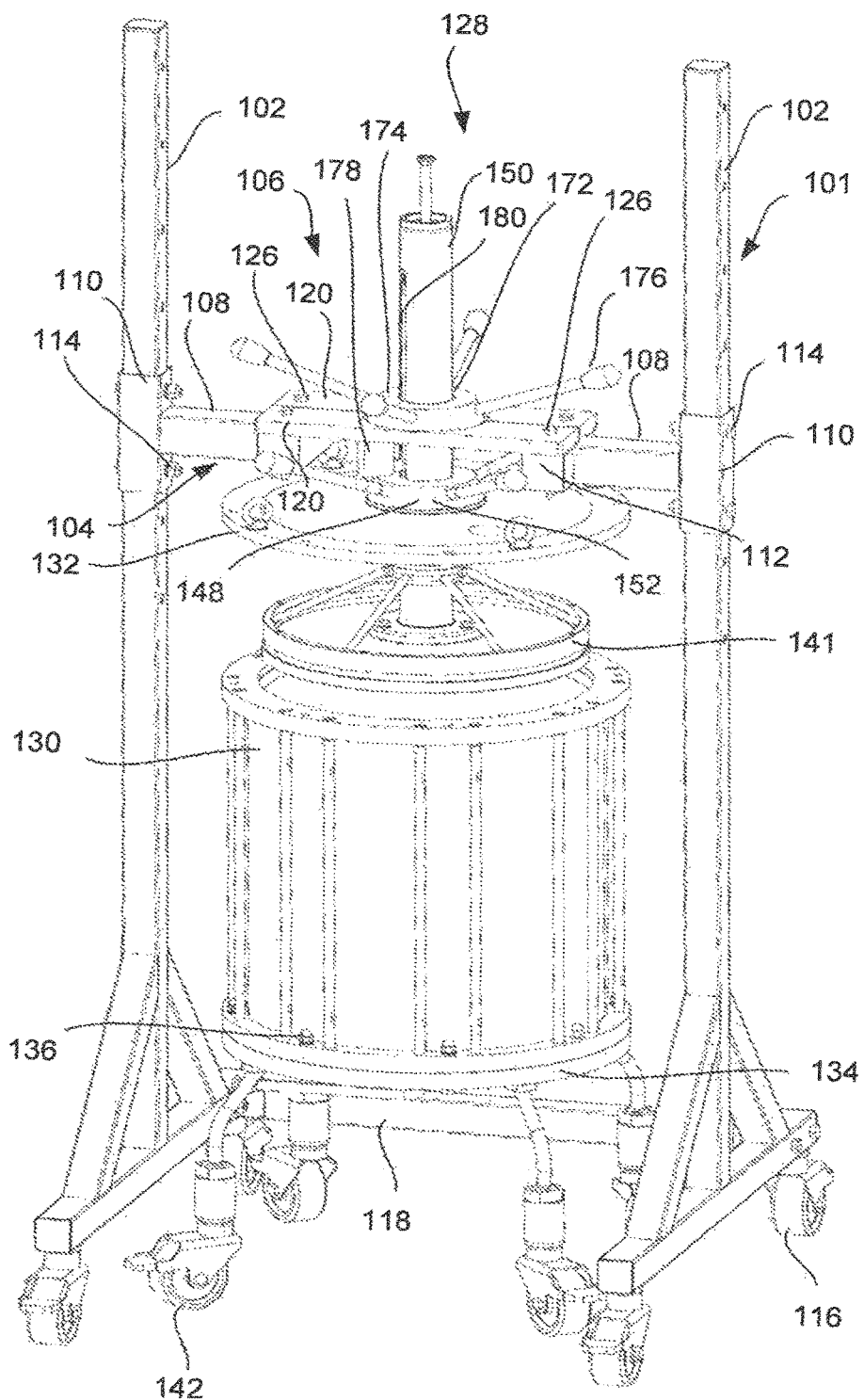
FIG. 6 shows a view in perspective of the chromatography column in FIG. 2 positioned in the frame according to FIG. 1, in which the first end unit and the adaptor assembly have been lifted from the tubular housing.

In FIG. 6 the first end unit 132 and the adaptor assembly 141 have been lifted vertically upwards from the tubular housing 130 by means of the threaded sleeve 174. Since the tubular housing 130 together with the second end unit 134 rest on supporting wheels 142 it is easy to withdraw the tubular housing 130 and the second end unit 134 from the frame 101. Alternatively, the frame 101 may be withdrawn from the tubular housing 130 and the second end unit 134 by means of the wheels 116 on the frame 101. The tubular housing 130 and the second end unit 134 may thereafter be displaced to a maintenance area, for replacing or cleaning the filter. Alternatively, the first end unit 132 and the adaptor assembly 141 may be displaced to a maintenance area for replacing or cleaning the filter.

Figure 7:
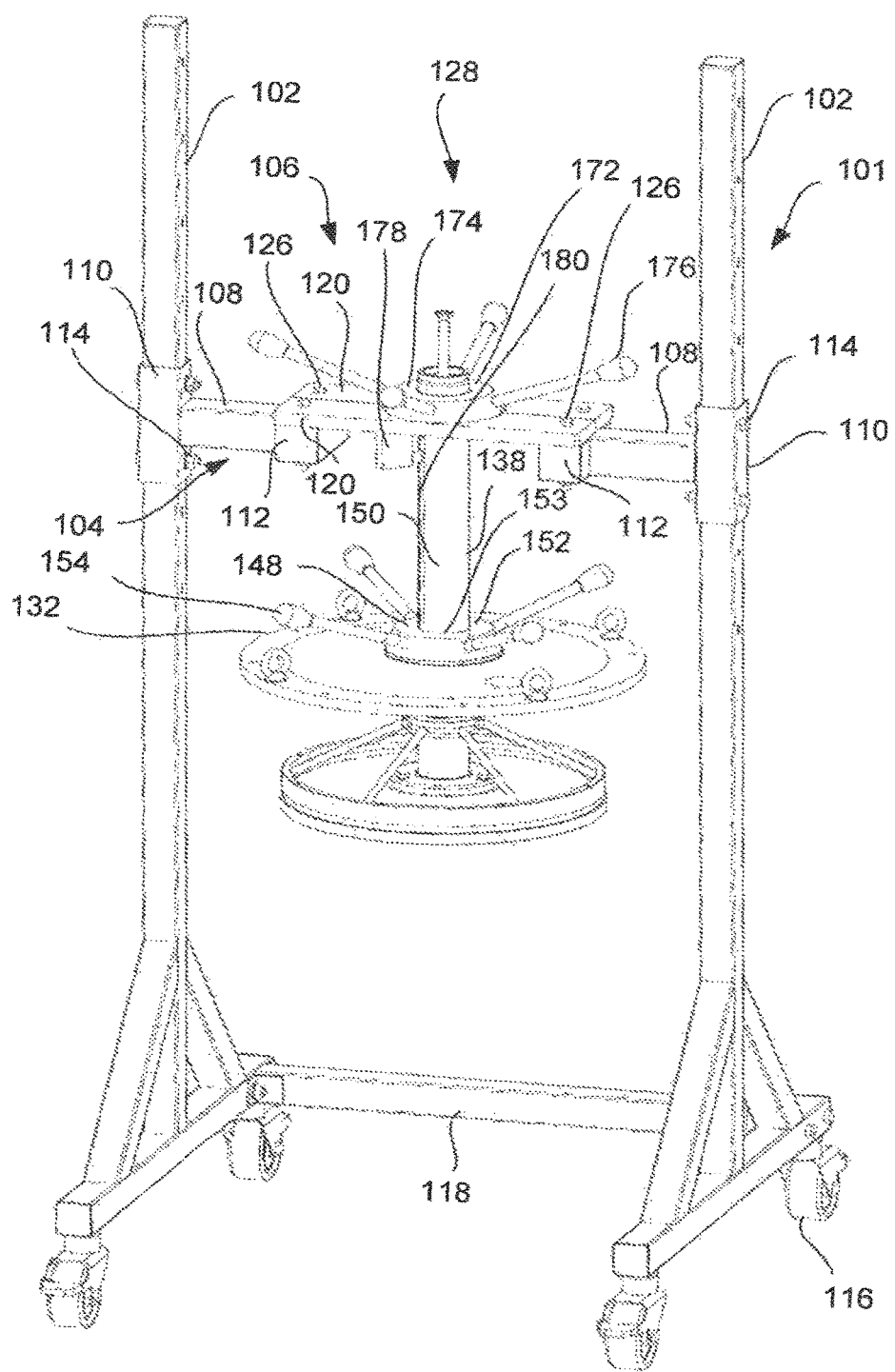
FIG. 7 shows a view in perspective of the frame in FIG. 1 in which the first end unit and the adaptor assembly are suspended in a holder means of the frame.

In FIG. 7 the frame 101 is disclosed in which the first end unit 132 and the adaptor assembly 141 are suspended. The tubular housing 130 has been removed, and it is easy to perform maintenance and service on the first end unit 132 and the adaptor assembly 141.

Figure 8:
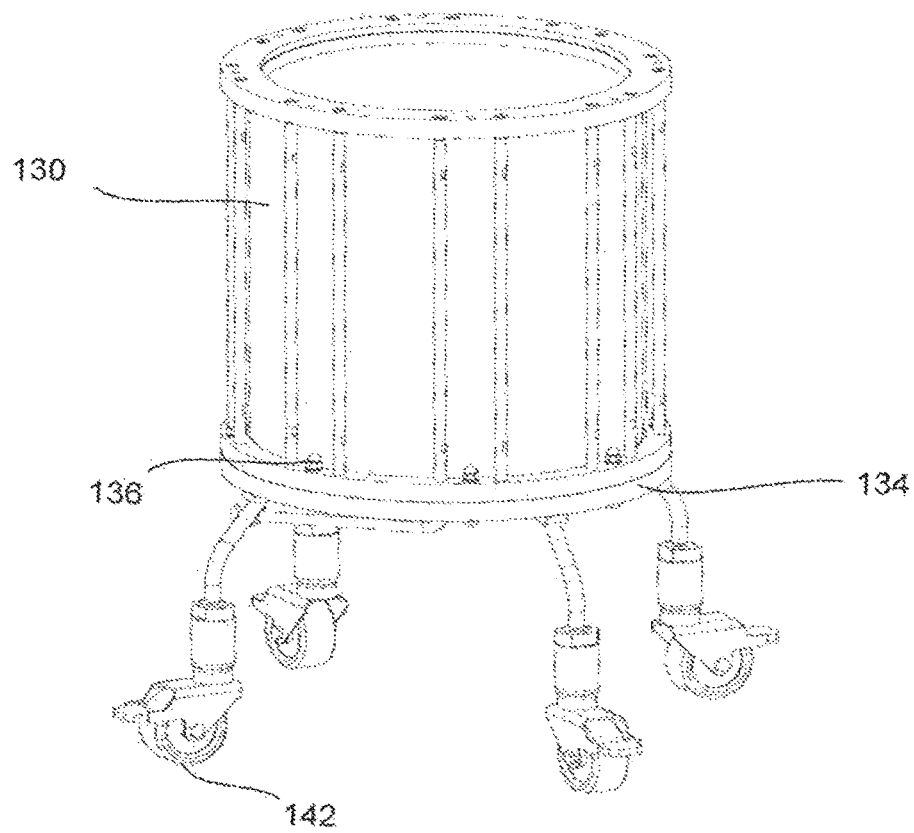
FIG. 8 shows a view in perspective of the tubular housing and the second end unit resting on wheels.

In FIG. 8 the tubular housing 130 together with the second end unit 134 resting on supporting wheels 142 are disclosed. In this position packing material may be supplied into the tubular housing 130. When packing material has been pumped or poured into the tubular housing 130, the tubular housing 130 together with the second end unit 134 rest are moved on the supporting wheels 142 back to the frame 101 and the driving means 172 is activated, so that the adaptor rod 138 together with the first end unit 132 and the adaptor assembly 141 move vertically downwards for positioning the first end unit 132 and the adaptor assembly 141 to and into the tubular housing 130. Thereafter, the first end unit 132 is connected to the tubular housing 130 and the packing material is compressed in the column 128 by means of the operating means 148 on the adaptor assembly 141.

Figure 9:
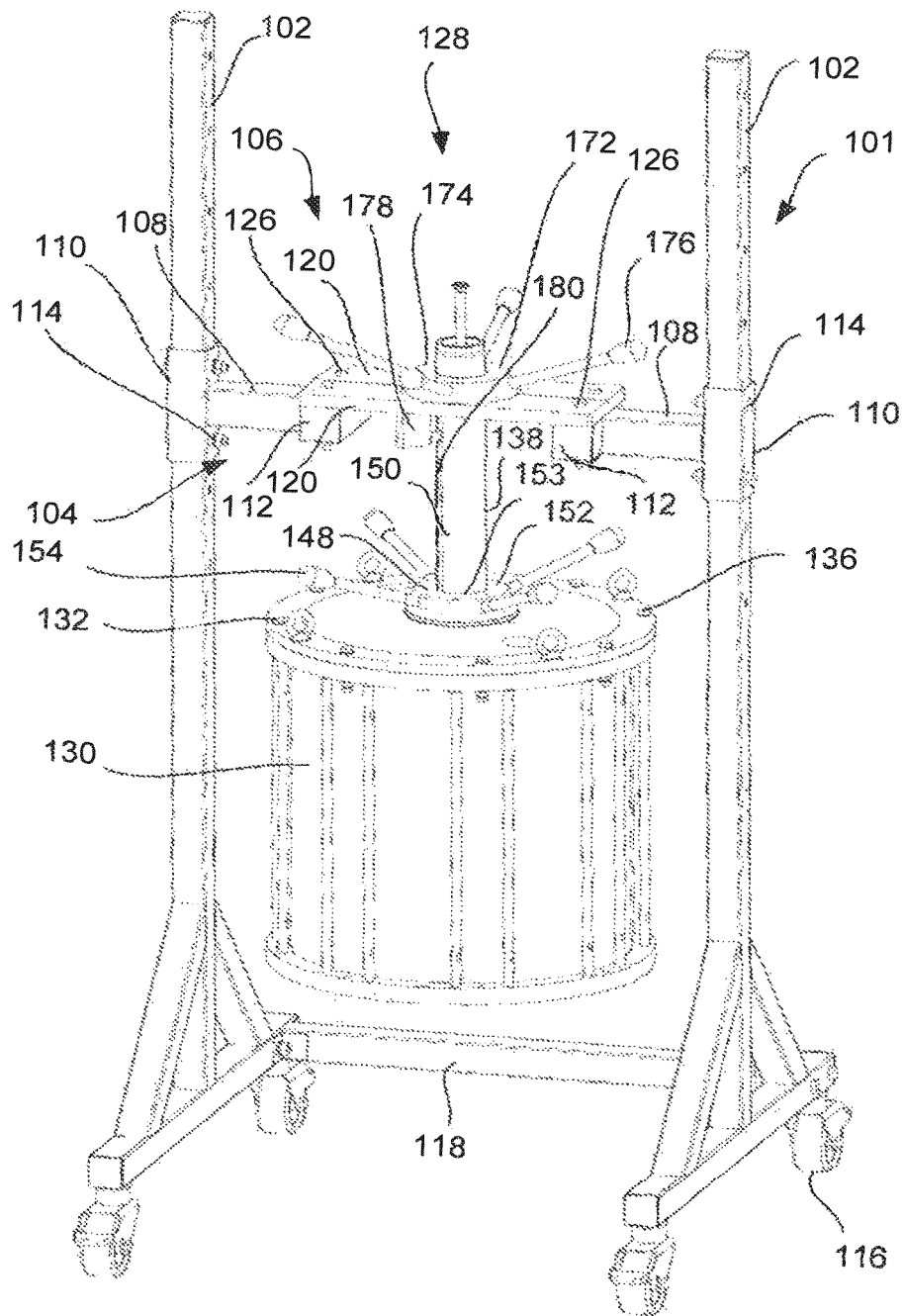
FIG. 9 shows a view in perspective of the frame in FIG. 1 in which the first end unit, the adaptor assembly and the tubular housing are suspended in the holder means of the frame.

FIG. 9 shows how the first end unit 132, the adaptor assembly 141 and also the tubular housing 130 have been lifted vertically upwards from the second end unit 134. Since the second end unit rests on supporting wheels 142 it is easy to withdraw the second end unit 134 from the frame 101. The second end unit 134 may thereafter be displaced to a maintenance area for replacing or cleaning the filter. Before the tubular housing 130 have been lifted vertically upwards from the second end unit 134, the tension bolts 160 which connect the second end 134 unit to the tubular housing 130 are removed.

Figure 10:
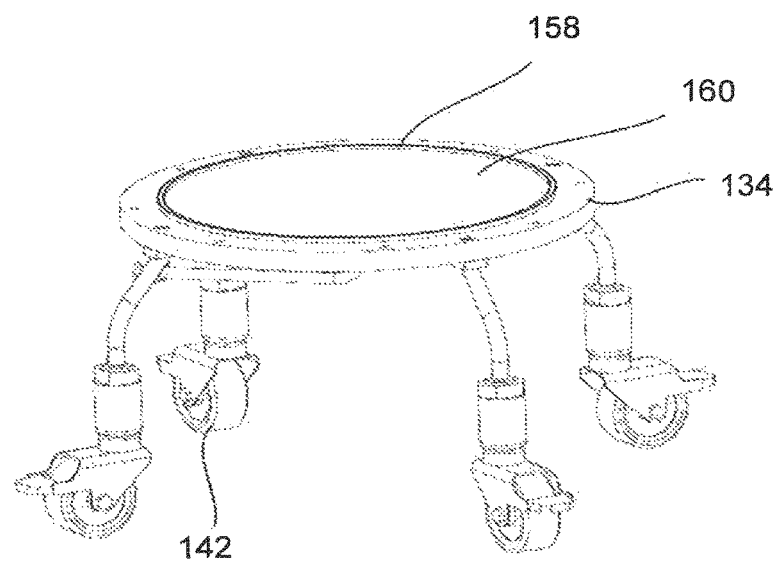
FIG. 10 shows a view in perspective of the second end unit resting on the wheels.

In FIG. 10 the second end unit 134 resting on supporting wheels 142 is disclosed. In this position it is easy to perform maintenance on the second end unit 134, such as replacing or cleaning the filter.

In all embodiments described above parts and surfaces being in contact with a process fluid are suitably selected from materials that are in accordance with typical material requirements in (bio-)pharmaceutical manufacturing or food grade quality.

For example, materials are suitably in compliance with USP Class VI and 21 CFR 177. Furthermore they are suitably of animal-free origin and compliance to EMEA/41O/01.

Features and components of the different embodiments above may be combined within the scope of the invention.

What is claimed is:

1. A method of conducting maintenance on and packing of a chromatography column, the method comprising:
   providing a chromatography column comprising:
      a tubular housing;
      a first end unit removably connected to a first end of the tubular housing;
      a second end unit removably connected to a second end of the tubular housing;
      an adaptor assembly moveable within said tubular housing;
      an adaptor rod connected to said adaptor assembly, wherein the adaptor rod is arranged to extend through an opening in the first end unit;
   providing a frame comprising:
      at least two legs;
      a support arrangement adjustably connected to said at least two legs to adjust in a horizontal direction based on a corresponding height of the chromatography column, wherein the adaptor rod extends through the first end unit and an opening of the support arrangement of a larger dimension that that of the adaptor rod to facilitate vertical movement of the adaptor rod; and
      a holder connected to said support arrangement and comprising a pair of separate support plates arranged thereon and each support plate of the pair of support plates comprising a recess which recesses together to define a substantially circular opening of the support arrangement wherein at least one support plate of the pair of support plates is removably connected to the support arrangement;
   disconnecting the first end unit or the second end unit from the tubular housing;
   positioning the adaptor rod in said holder, to block the adaptor rod from moving in a horizontal direction and to allow the adaptor rod to move in a vertical direction;
   arranging a driver on the adaptor rod; and
   activating the driver, to move the adaptor rod together with the first end unit and the adaptor assembly vertically upwards separating the first end unit and the adaptor assembly from the tubular housing and separating the tubular housing from the second end unit.

2. The method according to claim 1, further comprising: performing maintenance on the chromatography column.

3. The method according to claim 1, further comprising:
supplying a packing material into the tubular housing, when the tubular housing is connected to the second end unit.

4. The method according to claim 3, further comprising:
activating the driver, so that the adaptor rod together with the first end unit and the adaptor assembly move vertically downwards for positioning the first end unit and the adaptor assembly to and into the tubular housing;
connecting the first end unit to the tubular housing;
compressing the packing material in the chromatography column by the adaptor assembly.

5. The method according to claim 1, further comprising:
providing at least one support wheel in a position under the column.

6. The method according to claim 1, further comprising:
arranging a stopper on the support arrangement, thereby blocking the adaptor rod from pivoting in the holder via the stopper.

* * * * *